(12) United States Patent
Takei et al.

(10) Patent No.: US 8,607,783 B2
(45) Date of Patent: Dec. 17, 2013

(54) DRUG EJECTING APPARATUS AND CONTROL METHOD THEREOF

(75) Inventors: Masahiro Takei, Kawasaki (JP); Minoru Machida, Yokohama (JP); Satoshi Tsuchiya, Inagi (JP); Mitsuru Imai, Chichibu (JP); Keisuke Kawahara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 656 days.

(21) Appl. No.: 12/742,832

(22) PCT Filed: Jan. 20, 2009

(86) PCT No.: PCT/JP2009/051140
§ 371 (c)(1),
(2), (4) Date: May 13, 2010

(87) PCT Pub. No.: WO2009/093720
PCT Pub. Date: Jul. 30, 2009

(65) Prior Publication Data
US 2010/0282254 A1 Nov. 11, 2010

(30) Foreign Application Priority Data

Jan. 25, 2008 (JP) ................................. 2008-014458
Jun. 17, 2008 (JP) ................................. 2008-157987

(51) Int. Cl.
*A61M 11/00* (2006.01)
(52) U.S. Cl.
USPC .............................. 128/200.23; 128/200.24

(58) Field of Classification Search
USPC ............. 128/200.11, 200.23, 200.24, 203.12, 128/203.15, 202.17; 239/357, 326, 349, 239/354; 222/187, 383.1, 634
See application file for complete search history.

(56) References Cited

U.S. PATENT DOCUMENTS

| 4,767,416 A | * | 8/1988 | Wolf et al. | 604/239 |
| 5,098,386 A | | 3/1992 | Smith | 604/152 |
| 6,755,189 B2 | * | 6/2004 | Ivri et al. | 128/200.16 |

(Continued)

FOREIGN PATENT DOCUMENTS

| EP | 531257 A1 | 3/1993 | B65D 83/00 |
| JP | H06-079881 | 3/1994 | B41J 2/175 |
| JP | 2004-283245 | 10/2004 | A61M 11/00 |
| JP | 2004-290593 | 10/2004 | A61M 11/00 |

OTHER PUBLICATIONS

Office Action dated Feb. 14, 2012, issued in P.R.China counterpart application 200980102598.2, with translation.
Office Action issued Jan. 22, 2013 in counterpart Japanese Patent Application No. 2008-157987, with translation.

*Primary Examiner* — Steven Douglas
(74) *Attorney, Agent, or Firm* — Fitzpatrick, Cella, Harper & Scinto

(57) ABSTRACT

A drug ejecting apparatus has an ejection port and an element which generates energy for ejecting a drug from the ejection port; a drug containing unit is connected to the drug ejection apparatus, and contains the drug; a movable wall is attached to an end of the drug containing unit, and is displaced by difference between pressures inside and outside of the drug containing unit; and a control unit displaces the movable wall. The drug ejection apparatus is filled with the drug, and the inside pressure of the drug containing unit is put in a negative pressure state in advance of ejecting of the drug, by displacing the movable wall by means of the control unit.

6 Claims, 18 Drawing Sheets

(56) References Cited

U.S. PATENT DOCUMENTS

| | | | |
|---|---|---|---|
| 6,782,886 B2 * | 8/2004 | Narayan et al. | 128/200.14 |
| 7,195,011 B2 * | 3/2007 | Loeffler et al. | 128/200.14 |
| 2007/0062520 A1 | 3/2007 | Nobutani et al. | 128/200.14 |
| 2007/0227534 A1 | 10/2007 | Nobutani et al. | 128/200.14 |
| 2009/0188494 A1 | 7/2009 | Imai et al. | 128/203.12 |
| 2010/0043792 A1 | 2/2010 | Takei | 128/203.15 |
| 2010/0154793 A1 | 6/2010 | Kobayashi et al. | 128/203.14 |
| 2010/0206307 A1 | 8/2010 | Imai et al. | 128/203.14 |

* cited by examiner

DRUG EJECTING APPARATUS AND CONTROL METHOD THEREOF

TECHNICAL FIELD

The present invention relates to a drug ejecting apparatus which is constructed so that a user can use it while carrying it, and which can be used for an inhalation apparatus for making the user inhale a drug, and the like, and its control method.

BACKGROUND ART

There have been developed inhalation apparatuses which make and eject minute droplets of a drug using the ejection principle of an ink jet system, and make a user inhale them in an air flow path through which air inhaled through a mouthpiece flows (refer to Japanese Patent Application Laid-Open Nos. 2004-290593 and 2004-283245). Such inhalation apparatuses have an advantage of being able to spray a predetermined amount of drug precisely in an equalized particle diameter.

As the fundamental construction of such a drug ejecting apparatus, there are an ejection head in which an ejection energy generating element, such as a heat-generating element, is arranged, and a drug tank which contains the drug supplied to the ejection head. Here, in order to absorb efficiently medical fluid, which is ejected, in the lungs, it is important that the droplet diameter is extremely minute, as small as several microns, and, as for an orifice diameter of the ejection head, a dimension of several microns is therefore required.

In addition, in the field of ink jet recording apparatuses, a method of securing negative pressure in an ink tank by sucking an outside space of a flexible ink tank indirectly with a pump for negative pressure generation is known (refer to Japanese Patent Application Laid-Open No. H06-079881).

An ejection head, prior to be used for the first time, is not filled with the drug in a drug tank to the ejection port. In addition, also at the time of second or later use, a restoring operation of replacing the drug near the ejection port, to perform what is termed "refreshing", may be needed. In this point, it is common to perform suction with a vacuum pump from the outside of an orifice face of an ejection port in the field of ink jet recording apparatuses, and to perform a first-time filling operation and second-time and later restoring operations.

On the other hand, in the ink jet system, in order to perform proper ejection once an ejection head is filled with a drug, proper negative pressure must be secured inside the ejection head orifice. It turns out that, when an ejection port performs ejection with 3 μm of ejection head, it can be performed to maintain pressure inside an ejection head orifice in the range of −1 kPa to −5 kPa based on outside pressure. The pressure inside the orifice is almost equivalent to the inside pressure of the drug tank connected to the ejection head here.

The apparatus will be made larger by the inclusion of a suction pump, when filling and restoring operations are intended to perform with a suction pump, as is conventional, or where it is intended to secure negative pressure in a drug tank by the method described in Japanese Patent Application Laid-Open No. H06-079881. This is not suitable in a drug ejecting apparatus for which portability is required, such as an inhalation apparatus.

DISCLOSURE OF THE INVENTION

An object of the present invention is to provide a drug ejecting apparatus which can perform filling and restoring operations for a drug, which are performed before the ejection of the drug, and which may secure the desired initial negative pressure in using a simpler mechanism and operation.

The present invention is directed to a drug ejecting apparatus comprising:
a drug ejection apparatus which has an ejection port and an element which generates energy for ejecting a drug from the ejection port;
a drug containing unit which is connected to the drug ejection apparatus, and contains the drug;
a movable wall which is attached to an end of the drug containing unit, and is displaced by difference between pressures from the inside and outside of the drug containing unit; and
a control unit which displaces the movable wall, wherein the drug ejection apparatus is filled with the drug, and inside pressure of the drug containing unit is made into a negative pressure state in advance of ejecting of the drug, by displacing the movable wall by the control unit.

The drug ejecting apparatus can comprise an inhibition unit which inhibits ejection of a drug from the drug ejection apparatus before making the inside pressure of the drug containing unit into a negative pressure state by displacing the movable wall.

The drug ejecting apparatus can comprise a storage unit which stores the displacement amount of the movable wall for filling the drug into the drug ejection apparatus, and the displacement amount of the movable wall for making inside pressure of the drug containing unit into a negative pressure state, and the control unit displaces the movable wall based on the displacement amount stored in the storage unit.

In the drug ejecting apparatus the displacement amount of the movable wall can be made changeable according to drug residual amount inside the drug containing unit.

The drug ejection apparatus can eject the drug by means of the ejection principle of an ink jet system.

The present invention is directed to a control method of a drug ejecting apparatus which ejects a drug comprising:
a drug ejection apparatus which has an ejection port and an element which generates energy for ejecting a drug from the ejection port, and
a drug containing unit which is connected to the drug ejection apparatus and contains the drug, the method characterized by comprising:
making the drug ejection apparatus filled with the drug;
making inside pressure of the drug containing unit into a negative pressure state; and
ejecting the drug from the drug ejection apparatus.

A drug ejecting apparatus of the present invention permits adoption of a simple mechanism and operation while yet performing filling and restoring operations of a drug to the ejecting head, and securing initial negative pressure in the medicament container for performing ejection by the same pressure regulation mechanism. In consequence, miniaturization and cost reduction of the apparatus can be achieved, and a drug ejecting apparatus which is further suitable for a portable inhalation apparatus can be provided.

Other features and advantages of the present invention will be apparent from the following description taken in conjunction with the accompanying drawings, in which like reference characters designate the same or similar parts throughout the figures thereof.

BEST MODES FOR CARRYING OUT THE INVENTION

Figure 1:
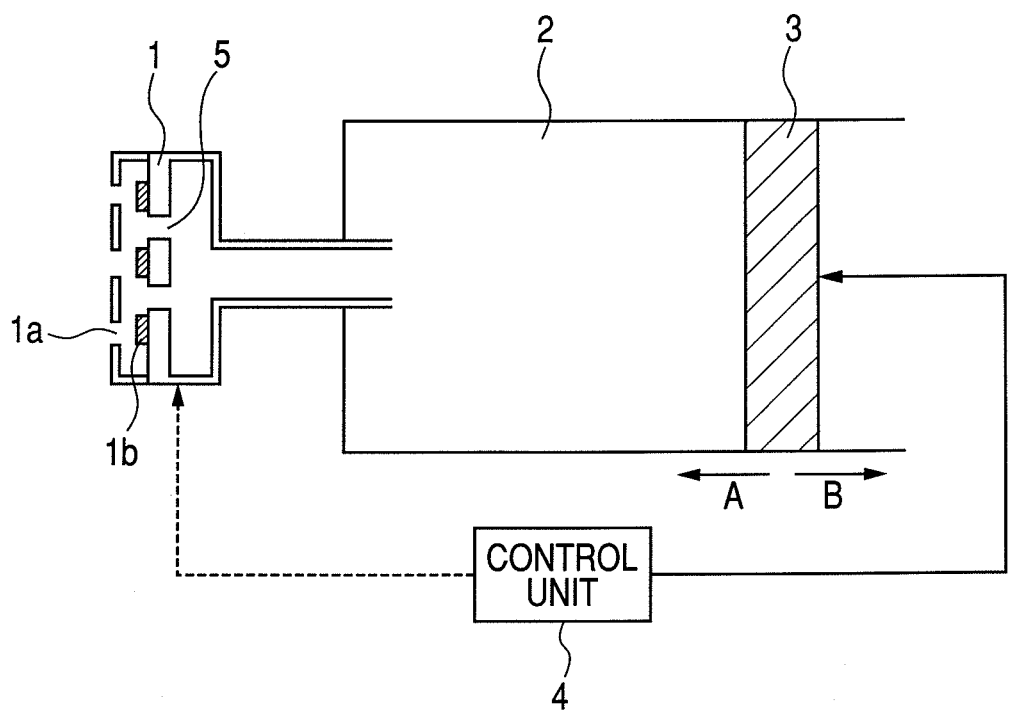
FIG. 1 is a diagram illustrating conceptually a part of a drug ejecting apparatus of the present invention.

Preferred embodiments of the present invention will now be described in detail in accordance with the accompanying drawings. In addition, the same reference numerals are assigned to the same components fundamentally, and their descriptions are omitted.

FIG. 1 is a diagram illustrating conceptually a part of a drug ejecting apparatus of the present invention. A drug ejection apparatus (ejection head unit) 1 is made of an ejection port (nozzle) 1a from which a drug is ejected, and an element 1b which generates energy for ejecting the drug from the ejection port 1a. The ejection energy generating element 1b gives ejection energy to the drug that has passed through a drug supply port 5. Thereby, the drug is ejected from the ejection port 1a.

The drug containing unit 2 which contains the drug which is ejected is connected to the drug ejection apparatus 1, and is isolated from the open air other than through the ejection port 1a. Therefore, the drug is ejected from the ejection port 1a, and when the amount of the drug contained in the drug containing unit 2 decreases, a differential pressure occurs between the inside and outside of the drug containing unit 2.

Here, a movable wall 3 displaced by the difference between pressures applied from the inside and outside of the drug containing unit 2 is attached to an end of the drug containing unit 2. The movable wall 3 is slidable relative to the drug containing unit 2, and makes the volume of the drug containing unit 2 changeable. In consequence, the inside pressure of the drug containing unit 2 is maintained at a predetermined value. Then, the inside pressure of the drug containing unit 2 is controllable by displacing the movable wall 3 positively by the control unit 4. Specifically, when the movable wall 3 is displaced in a direction (direction A in FIG. 1) in which the volume of the drug containing unit 2 is reduced, the inside pressure of the drug containing unit 2 increases. In addition, when the movable wall 3 is displaced in a direction (direction B in FIG. 1) in which the volume is increased, the inside pressure of the drug containing unit 2 is reduced. The displacement of the movable wall 3 can be performed by means of the control unit 4.

An outline is described although the specific construction of the drug containing unit (drug tank) 2 will be described with reference to the below-mentioned embodiment. A main body of the device can be made of a glass container with both ends open in the drug tank, and one end can be plugged with a member, such as a rubber stopper, as the movable wall 3. The other end is connected to the ejection head unit 1. If the rubber stopper is slidably displaced toward an inside of the glass container, container inside pressure increases.

In order to eject a drug, the drug in the drug containing unit 2 must be sufficiently filled to the ejection port 1a of the drug ejection apparatus 1. Then, in advance of ejection, an operation of filling the drug in the drug containing unit 2 into the drug ejection apparatus is needed. In the present invention, the movable wall 3 is displaced by a predetermined amount in the direction A by the control unit 4. In consequence, the inside of the drug containing unit 2 becomes in a positive pressure state, the drug is filled into the drug ejection apparatus 1 as being pushed out. (This operation is hereafter called a "filling operation" in this specification.)

In this specification, "filling" includes not only filling a drug starting from a state in which the ejection head unit 1 is empty to a state in which the drug is filled to the ejection port 1a, at the time of first time use of the ejection head unit 1, but also filling a new drug to the ejection port 1a at the time when the drug is already filled. When the drug has been already filled, an operation of refreshing the drug in this way may be called a "restoring operation."

After the filling is completed, in order to eject the drug properly from the ejection port 1a by the element 1b when ejection is started, it is necessary to make a space inside the ejection port 1a have a predetermined negative pressure. The term "predetermined negative pressure" means a pressure lower than the open air to a sufficient extent that a meniscus which is needed to eject liquid and form flying liquid droplets is maintained. Specifically, it is selected from the range of −1 kPa to −5 kPa relative to the outside pressure of the ejection head. Then, the movable wall 3 is displaced by a predetermined amount in the direction B by the control unit 4. In consequence, the inside of the drug containing unit 2 assumes a negative pressure state. Since the drug containing unit 2 is connected to the drug ejection apparatus 1, this inside pressure is almost equivalent to the pressure of the inner space of the ejection port 1a. Therefore, proper ejection is achievable. This operation is hereafter called an "initial negative pressure securing operation" in this specification.

After causing the inside pressure of the drug containing unit 2 to be in the proper negative pressure state, the element 1b is driven and the drug is ejected. In order to maintain the predetermined negative pressure during the ejection, it is suitable to displace the movable wall 3b in the direction A according to reduction of the amount of drug remaining in the drug containing unit 2. For this reason, drive the element 1b may be driven to achieve synchronization of the displacement of the movable wall 3b, by the controlling control unit 4. In addition, the ejection may be a main ejection which ejects the drug used for a user's inhalation, or may be a "preliminary ejection", which serves to confirm the proper ejection state in advance of the main ejection.

In addition, since it is not suitable to perform ejection of a drug without performing operations of filling and initial negative pressure securement, before the above-mentioned operation is performed, it is suitable to provide inhibition means for inhibiting ejection. Specifically, before the above-mentioned operation is performed, a control flow of inhibiting the ejection is incorporable into firmware in the control unit 4.

Next, the displacement amount of the movable wall 3 in the direction A or the direction B at the time of performing the filling operation or initial negative pressure securing operation will be described. Since the sum total of the volume of a communicating vessel connected to the ejection head unit 1 from the drug tank 2 and the volume of an inside space of the ejection head unit 1 is known, also the displacement amount of the movable wall 3 necessary for the filling operation is known in one-to-one correspondence. In addition, the displacement amount for achieving the needed predetermined negative pressure state the container inside pressure after the filling operation is known. Therefore, it is suitable to have a storage unit which stores this displacement amount beforehand, and for the control unit 4 to displace the movable wall 3 based on that stored information. Thereby, since it becomes unnecessary to provide a pressure sensor for measuring the inside pressure of the drug tank 2 in-situ, simpler construction can be achieved.

When the movable wall 3 is displaced for an initial negative pressure securement in the same distance each time in the direction B and volumes of the drug tank 2, that is, drug residual amounts differ from each other, and the pressure fluctuations which are generated also differ. Therefore, it is suitable to secure the same (i.e., a consistent) negative pressure state by making the displacement amount of the movable wall 3 changeable each time according to the drug residual amount inside the drug containing unit. Specifically, it can be performed to store the displacement amount necessary for a drug residual amount beforehand to perform displacement based on the drug residual amount measured just before the initial negative pressure securing operation.

Here, the drug ejection apparatus (ejection head) 1 has an arbitrary ejection energy generating element. It can be performed to exemplify an electrothermal transducer which imparts heat energy to a drug, or an electromechanical transducer which imparts mechanical energy to a drug. That is, as ejection methods of a drug, it can be performed to exemplify a method (thermal ink jet system) of imparting heat energy to a drug and making it ejected using an electrothermal transducer, and a method (piezo-ink jet system) of ejecting a drug using oscillating pressure of an electromechanical transducer (piezoelectric element) which imparts mechanical energy to the drug. As for the ejection methods, it is selectable according to a type of a drug, or the like. The term "ink jet system" in this specification does not mean that ink is what is ejected, but is used to refer to ejecting a drug using the ejection principle of the system concerned.

When a thermal ink jet system is used, to enhance size accuracy and repeatability of an aperture of an ejection port, heat amount of a thermal pulse used for ejection, a microheater is provided as an electrothermal transducer for to each ejection head. For this reason, it can be performed to achieve a narrow droplet diameter distribution. In addition, the head manufacturing cost is low and applicability of the design to small apparatuses which need frequent exchange of a head is also high. Hence, for the drug ejecting apparatus to have the desired portability or convenience, in particular, it is suitable to adopt an ejection principle of a thermal ink jet type.

The drug used for the present invention may in concept not only be a drug such as a medicinal compound which shows a pharmacological and physiological operation, but may also be a component intended to provide a seductive taste and a seductive smell, or a dyestuff, a pigment, and the like. In addition, an arbitrary additive agent may be included.

(Drug Ejecting Apparatus)

FIG. 2 is a perspective view illustrating appearance of an inhaler which is an example of the drug ejection apparatus of the present invention and makes a user inhale a drug. A protective main body is formed by a housing case 17 and an access cover 18. Reference numeral 40 denotes a lock release button of the access cover. A construction in which a hook portion 19 (FIG. 4) provided so that the access cover 18 may not open in use is caught by a hook holding shaft which operates integrally with a lock release button 40 energized by a spring is adopted. This is constructed so that, when the access cover 18 is opened, a catch of the hook may be released by the release button 40 being pushed and the access cover 18 may open by the force of a spring (not shown) energizing it in an opening direction. A display unit 15 for displaying a dose, time, an error, and the like is provided in the access cover 18. In addition, a menu switching button 11 for a user to perform setting, an up button 12 and a down button 13 which are setting buttons, and a determination button 14 are provided.

FIG. 3 illustrates a state in which the access cover 18 is open in the inhaler in FIG. 2. When the access cover 18 opens, the ejection head unit 1 as a drug ejection apparatus which is detachable from the apparatus body, and the drug tank 2 as a drug containing unit appear. The ejection head unit 1 ejects the drug toward an air flow path 7. By breathing in from an inlet (mouthpiece) 20, a user can inhale the drug which is ejected into the air flow path. In this embodiment, the inlet 20 and air flow path 7 are sectioned. The inlet 20 is thrown away upon every inhalation, or it may be washed after inhalation and re-used. The ejection head unit 1 and drug tank 2 will be exchanged when the amount of drug remaining in the drug tank 2 becomes less than the amount of drug to be administered as a single dose. For example, since a function of counting ejection amount is done in the main body and the residual amount is computable by this ejection amount count function, notification of exchange time can be also performed to prompt a user to exchange the drug supply, or not to perform ejection until exchange is completed. Reference numeral 31 denotes a drive unit protective cover so that the user is unable to touch the inside mechanism of the inhaler easily.

(Ejection Head Unit and Drug Tank)

FIGS. 4, 5 and 6 illustrate an example of specific construction of the ejection head unit 1 and drug tank 2 which are used for the drug ejecting apparatus of the present invention.

FIG. 4 is a perspective view illustrating appearance of the ejection head unit 1 and drug tank 2. In addition, FIG. 5 is a principal sectional view of FIG. 4, and illustrates a state before the drug tank 2 is connected to the ejection head unit 1. FIG. 6 is a sectional view after the connection.

The ejection head unit 1 is made of the following components. That is, an ejection head 8 in which two or more ejection ports are arranged is attached to and supported by a housing 39, and a hollow needle 38 for supplying the drug to the ejection head 8 from the drug tank is arranged inside the housing. A medical fluid pass 42 which guides the drug 32 to the ejection head 8 through the hollow needle 38 branches to a pressure detection opening 23 on the way, and makes measurable the inside pressure generated in the medical fluid pass 42. In the pressure detection opening 23, a sealant 22 for preventing a pressure leak when being connected to a pressure sensor 43 (FIG. 8) after a main body is provided. After communication, since pressure in the medical fluid pass is almost equal to the pressure in the glass container, the pressure in the drug tank can be measured in this construction.

A heater, which is an ejection energy generating element, is provided near the ejection port in the ejection head 8, and heated drug is ejected from the ejection port with foaming energy. An electrical connection surface 9a for supplying electric power and an electric wiring part 9 which supports it also are in the heater. Electric power is supplied from a battery 29 (FIG. 8) which can be charged as a rechargeable battery which is held in the main body of the inhaler through the electrical connection surface 9a.

In order to protect the ejection head 8 before mounting it in the main body, a head protective lever 21 which has a medical fluid absorber 35 so as to contact an ejection port surface of the ejection head 8 is arranged. This is made to retreat so that the ejection port and an air flow path may communicate with each other at the time of ejection.

The drug tank 2 is made of the following components. That is, there is a glass container 33 for containing a drug, and in an end of the glass container 33, a fixed rubber stopper 36 is held down by a caulking metal fitting 37 made from aluminum. Then, in the other end of the glass container 33, a moving rubber stopper 34 as a movable wall is inserted into an inside of the container, and isolates the drug from the open air. In a phase that the drug tank 2 is connected to the ejection head unit 1, an inside of the glass container is isolated from the open air besides the ejection port of the ejection head 8. Sealing property of the drug tank is maintained by this construction, and denaturation and a concentration change of the drug are suppressed to the minimum.

Figure 6:
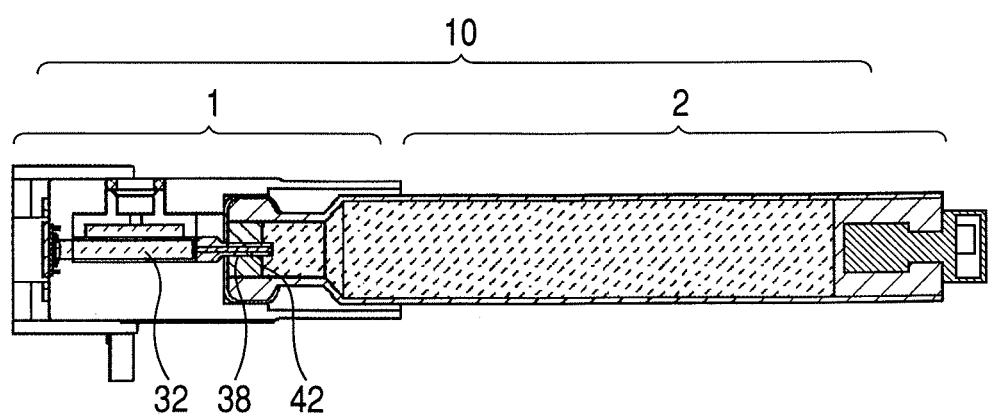
FIG. 6 is a sectional view after the ejection head unit 1 and drug tank 2 are connected.

As illustrated in FIG. 6, the drug tank 2 is pushed into the ejection head unit 1, the hollow needle 38 breaks through the fixed rubber stopper 36, and the ejection head unit 1 and drug tank 2 are communicated. Filling of the drug 32 into the ejection head 8 is performed by pushing the moving rubber stopper 34.

In order to make a user easily mount an inhalation apparatus body, before the drug tank 2 is connected to the ejection head unit 1, it is suitable for these to construct the drug cartridge 10 as one body.

(Inside of Apparatus Body)

Figure 2:
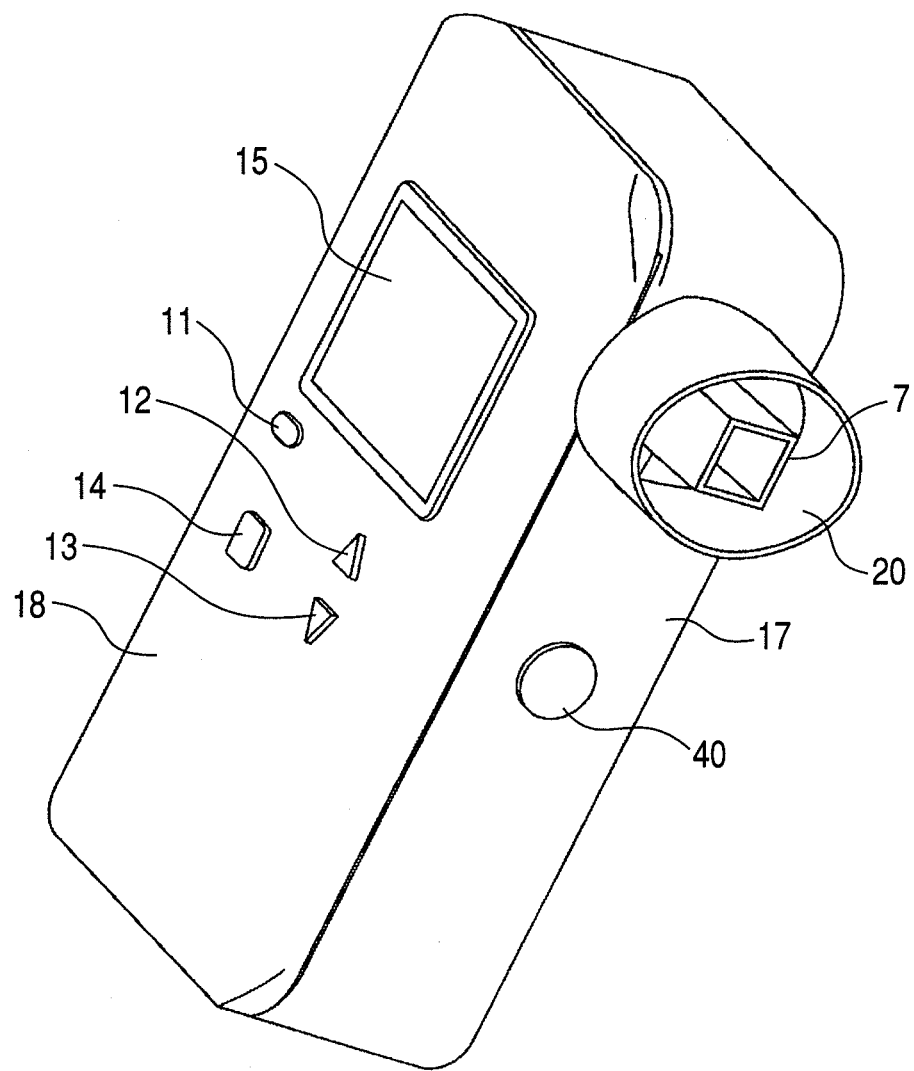
FIG. 2 is a perspective view illustrating appearance of an inhaler which is an example of the drug ejection apparatus of the present invention and makes a user inhale a drug.
Figure 3:
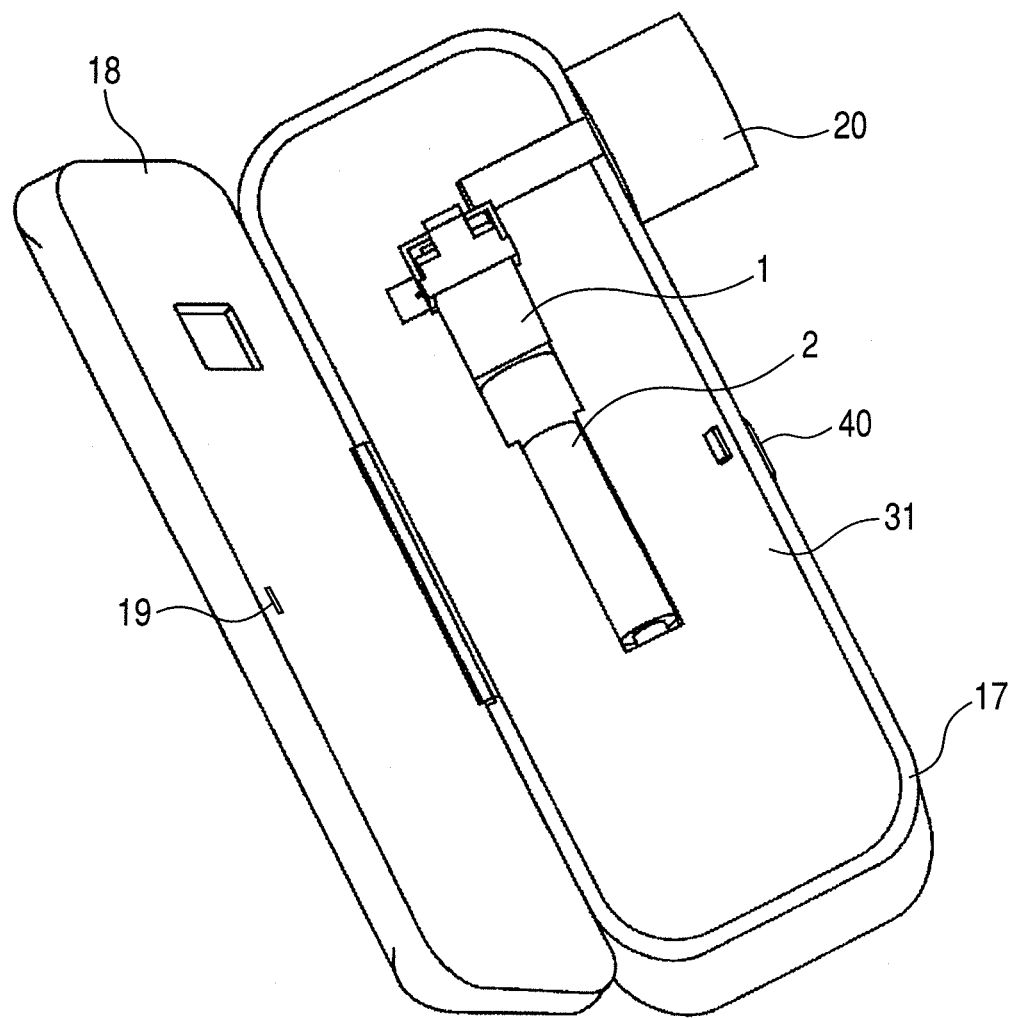
FIG. 3 illustrates a state in which an access cover 18 is open in the inhaler in FIG. 2.
Figure 4:
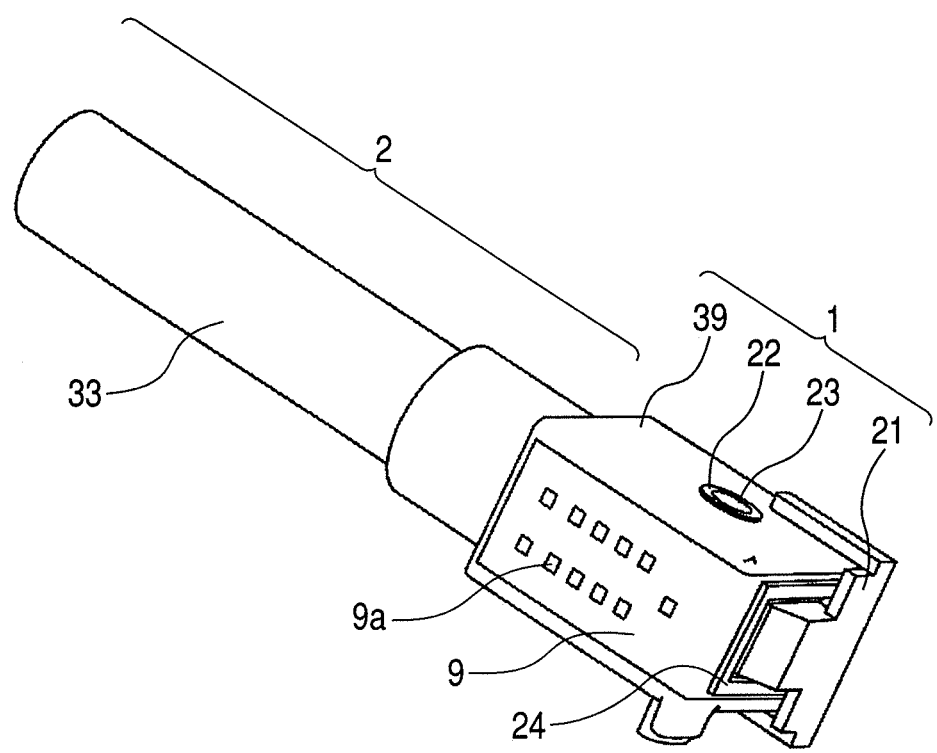
FIG. 4 is a perspective view illustrating appearance of an ejection head unit 1 and a drug tank 2.
Figure 5:
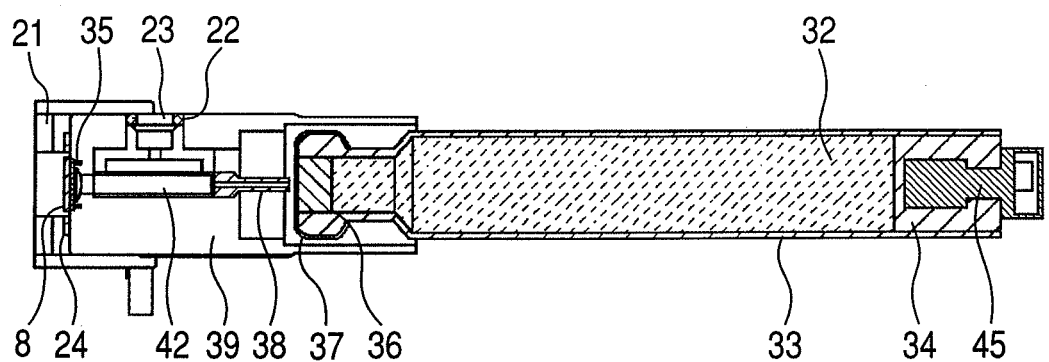
FIG. 5 is a principal sectional view of FIG. 4, and illustrates a state before the drug tank 2 is connected to the ejection head unit 1.
Figure 7:
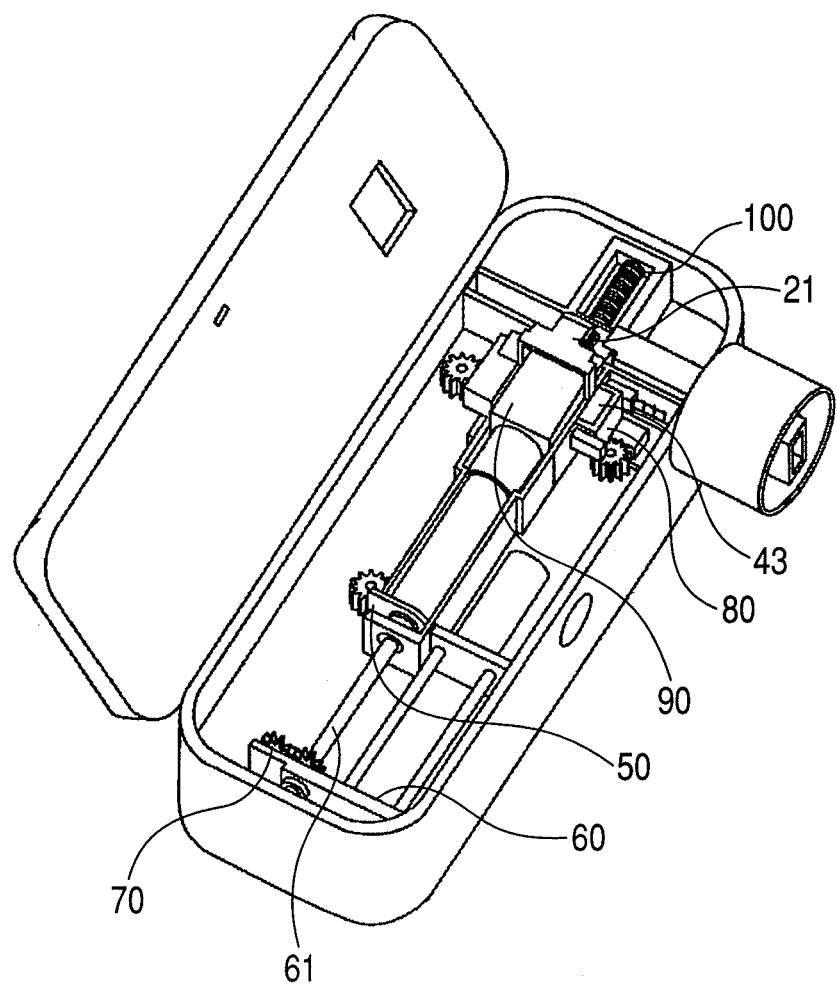
FIG. 7 is a perspective view showing a drive unit protective cover 31 removed, in FIG. 3, and showing the inside of the apparatus.

FIG. 7 is a perspective view at the time of removing a drive unit protective cover 31 in FIG. 2, and looking at an inside of the apparatus.

First, there is a pushing unit 50 for making the drug tank 2 connected to the ejection head unit 1, and making the drug pass 42 formed. Then, a moving rubber stopper moving unit 60 which moves the moving rubber stopper 34 to an opposite side in the glass container 33, sandwiching the drug tank 2, to make the interior volume of the drug tank 2 changeable is arranged. A piston pin is moved by driving and rotating a screw shaft motor 64 (FIG. 8) which has a screw shaft of the moving rubber stopper moving unit 60. There is a piston pin rotating unit 70 for performing a hooking operation of the moving rubber stopper joint 45 and piston pin 61 so as not to come out in a drawing operation. Furthermore, there is a pressure sensor connecting unit 80 for connecting the pressure sensor 43 to a pressure detection opening 23 first in both sides of a drug cartridge 10 (an article into which the ejection head unit 1 and drug tank 2 are packed). Then, a head protective lever retreating unit 90 for moving the head protective lever 21 which has protected the ejection head 8 and opening an ejection surface is arranged. A head capping unit 100 for preventing the ejection head 8 from drying and dust adhering in a state that the ejection head 8 is mounted in the main body is provided in an upper direction of the ejection head.

Figure 8:
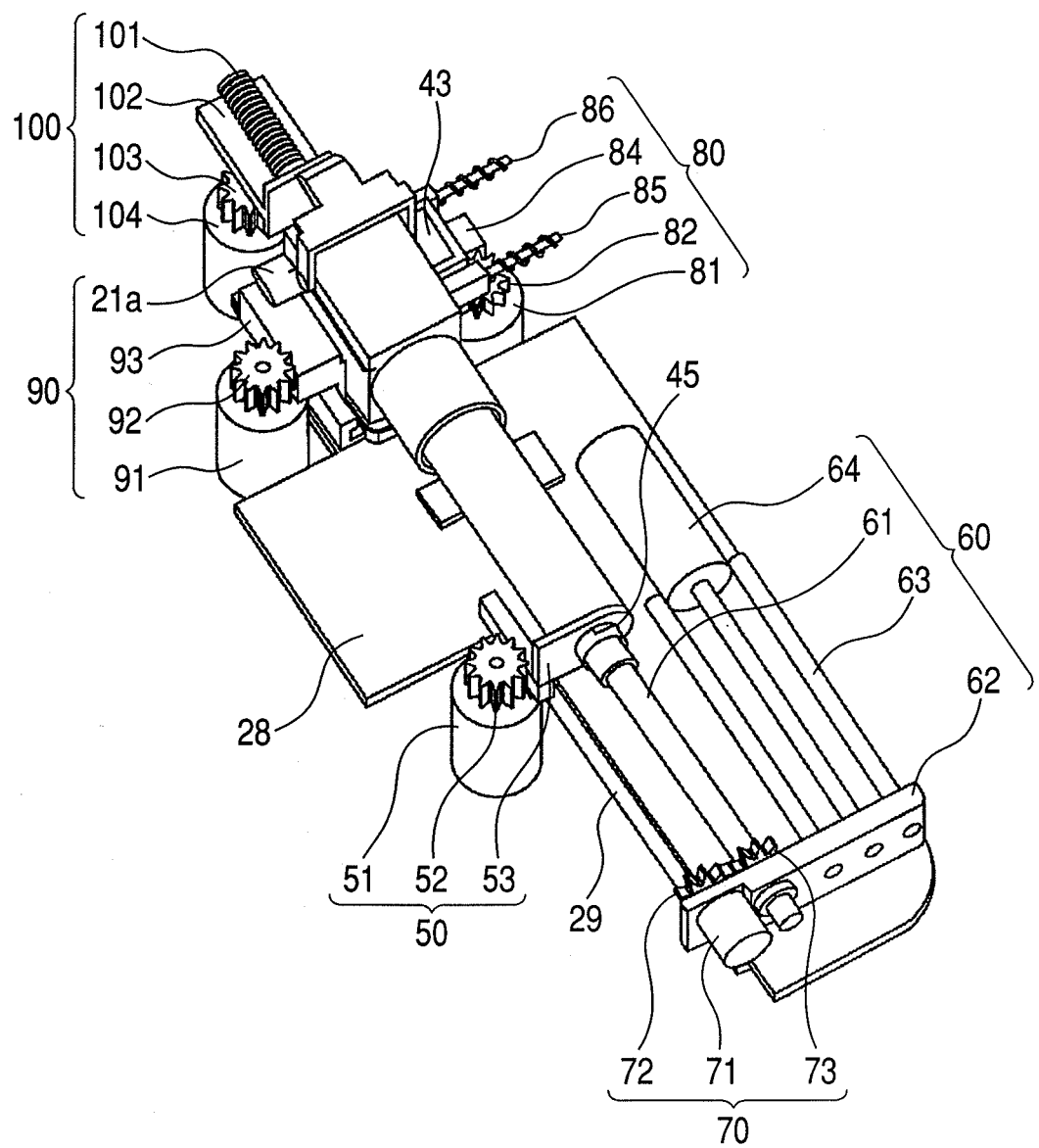
FIG. 8 is a diagram illustrating a mechanism inside the main body.

FIG. 8 is a diagram illustrating a mechanism inside the main body with removing all armours in FIG. 7. The pushing unit 50 is constructed of a motor 51 which generates a driving force which pushes in the drug tank, a pinion 52 press-fit into a motor shaft of the motor 51, and a pushing rack plate 53 which has in part a rack form which engages with the pinion 52. The rack plate 53 is arranged so as to push a rear edge of the glass container 33.

Next, the moving rubber stopper moving unit 60 will be described. It is inserted in a piston pin bearing clip 62 which has a female screw with which a thread shape of a screw of the screw shaft motor 64 which has a screw in a motor main shaft coincides. Guide shafts 63 are arranged in both sides of the screw shaft, and perform braking of the piston pin bearing clip 62 and guidance at the time of sliding. Therefore, a rotational driving force of the screw shaft motor 64 can perform slide movement of the piston pin 61, and can move the moving rubber stopper 34 connected through a moving rubber stopper joint 45.

A piston pin reversal unit 70 is built in the piston pin bearing clip 62. The piston pin reversal unit 70 can transmit a driving force of a piston pin reverse motor 71 and a reverse motor gear 72 press-fit in the motor main spindle to a piston gear 73, and can rotate the piston pin. Drug volume or inside pressure inside a glass tube is made adjustable by engaging the piston pin 61 and moving rubber stopper joint 45 by rotation of the piston gear 73 and pushing and drawing the moving rubber stopper 34 to the glass container 33.

In addition, a control base 28 is arranged under the drug cartridge 10, and in order to perform control of respective drive motors, main body control of drive of the ejection head, and the like, a CPU, ROM, and RAM are provided as the control unit 4 on the control base.

Furthermore, since it has construction that a battery 29 as a drive source of respective drive motors and an energy source for ejection is arranged under the control base 28, and ejection and inhalation of a drug can be performed only by this main body, it is made usable easily anywhere.

The pressure sensor connecting unit 80 will be described. This unit performs movement of the pressure sensor 43 for communication with and release from the pressure detection opening 23 which is provided in the housing 39. This has a connecting rack 84 which has a rack form that can convert into slide movement a turning force of a connection motor gear 82 press-fit into the motor main shaft in order to slidably moving a driving force of the motor 81. This performs drive transfer to the connecting rack 84 having a holding unit of the pressure sensor 43, and slidingly moves it in a direction of leaving from the housing 39. Thus, the motor 81 is used for releasing connection. In addition, connection is performed as follows. That is, it is press-connected by spring pressure of a pressure sensor connection pressure spring 86 which is built in an outer periphery of a connecting rack guide shaft 85 which performs guidance at the time of movement of the connecting rack 84. This is for securing that the pressure sensor 43 may not release the connection even if a body power supply is shut off, and thereby, it can be performed to monitor the drug tank inside pressure in a storage condition at the time of no use.

The head protective lever retreating unit 90 will be described. A pinion 92 press fit on a main spindle of the motor 91 and the protection lever rack 93 which has a rack form engage with each other. Then, the protection lever rack 93 slidingly moves, it strikes up a protruding portion 21a for retreat provided in an end portion of the head protective lever 21, the head protective lever 21 rotates, and the ejection head 8 is exposed. The head protective lever retreating unit 90 is driven only at the time of attach a drug cartridge.

The head capping unit 100 will be described. By a driving force of a motor 104, sliding of a capping plate 102 is enabled through a pinion 103 press fit into a motor shaft. It engages with a rack built in to a bottom face of the capping plate 102, and slidingly moves. Drive of the capping motor 104 is used only at the time of retreat of the capping plate 102. Capping of the ejection head 8 is performed by a pressing force of a capping spring 101. It is for capping even when the body power supply is OFF. Thus, only when ejection from the ejection head 8 is performed, the head capping unit 100 is made to be driven and capping is performed for prevention from drying besides the time of drug ejection.

(Block Diagram of Inhalation Apparatus)

Figure 9:
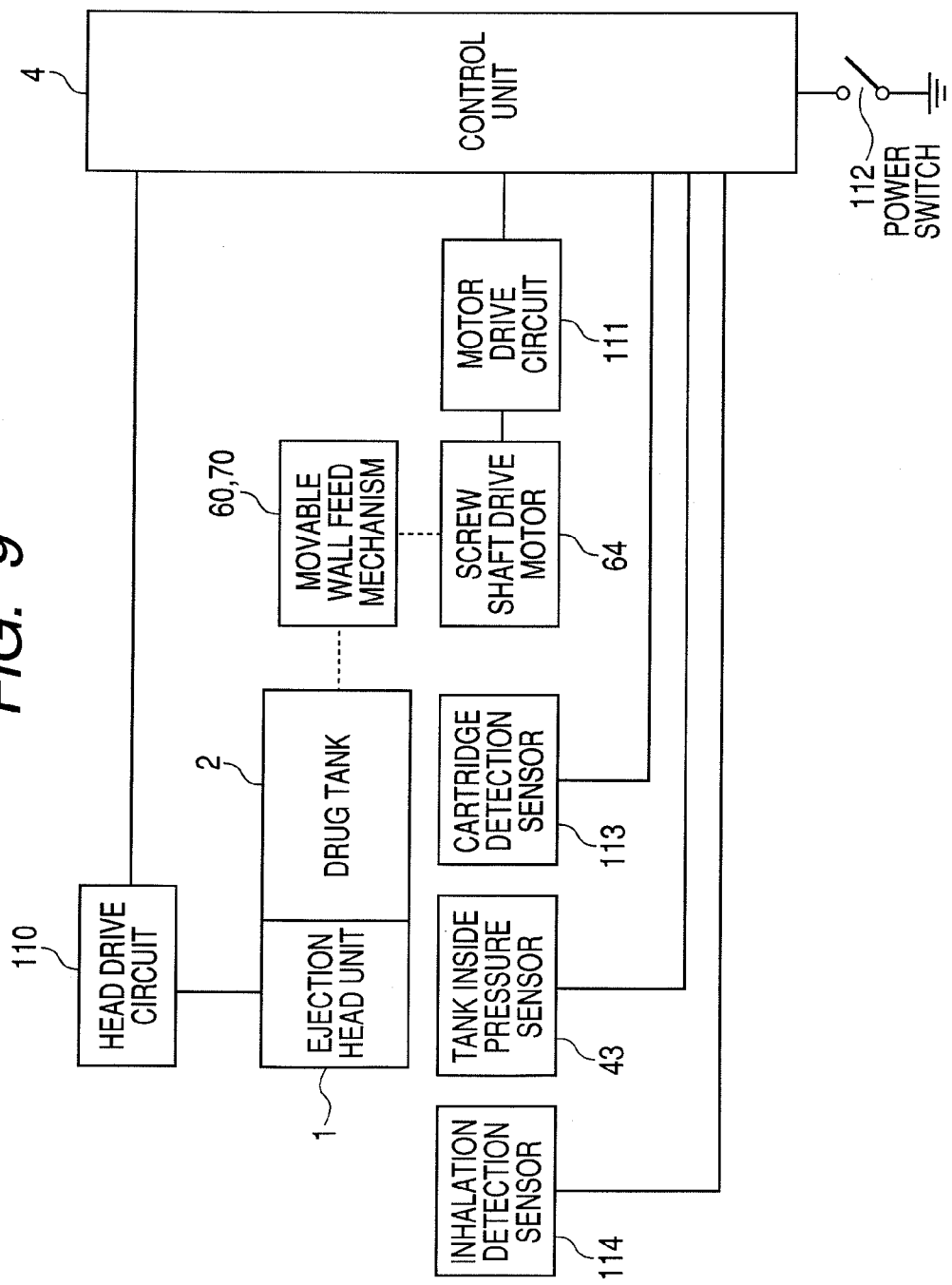
FIG. 9 is a block diagram of an inhaler according to a first embodiment of the present invention.

FIG. 9 is a block diagram of an inhaler according to a first embodiment of the present invention illustrated in FIGS. 2, 3, 4, 5, 6, 7 and 8.

A cartridge detection sensor 113 which detects that the drug cartridge into which the ejection head unit 1 and drug tank 2 are sectioned is mounted in the inhalation apparatus body is connected to the control unit 4. In addition, in order to perform drug spraying, a head drive circuit 110 for giving a drive signal to a heater is connected through an electrical connection surface 9a (FIG. 4) to the ejection head unit 1. The head drive circuit 110 is constructed of a gate array, such as an ASIC, and is designed so as to execute necessary spraying by itself with control data and an activation signal from the control unit 4.

The pressure sensor 43 which measures the tank inside pressure mentioned above is connected to the ejection head unit 1, and a measurement result here is sent to the control unit 4. In addition, the screw shaft motor 64 in a movable wall feed mechanism (60 and 70 in FIG. 8) is driven by a motor drive circuit 111 controlled by the control unit 4. The motor drive circuit 111 is constructed of a gate array similarly to the head drive circuit 110.

Furthermore, an inhalation detection sensor 114 which detects that a patient performs inhalation from the inlet 20 is connected to the control unit 4. In addition, a power switch 112 for turning a power source of the apparatus ON or OFF eventually is connected.

(Example of Use of Inhalation Apparatus)

Figure 10:
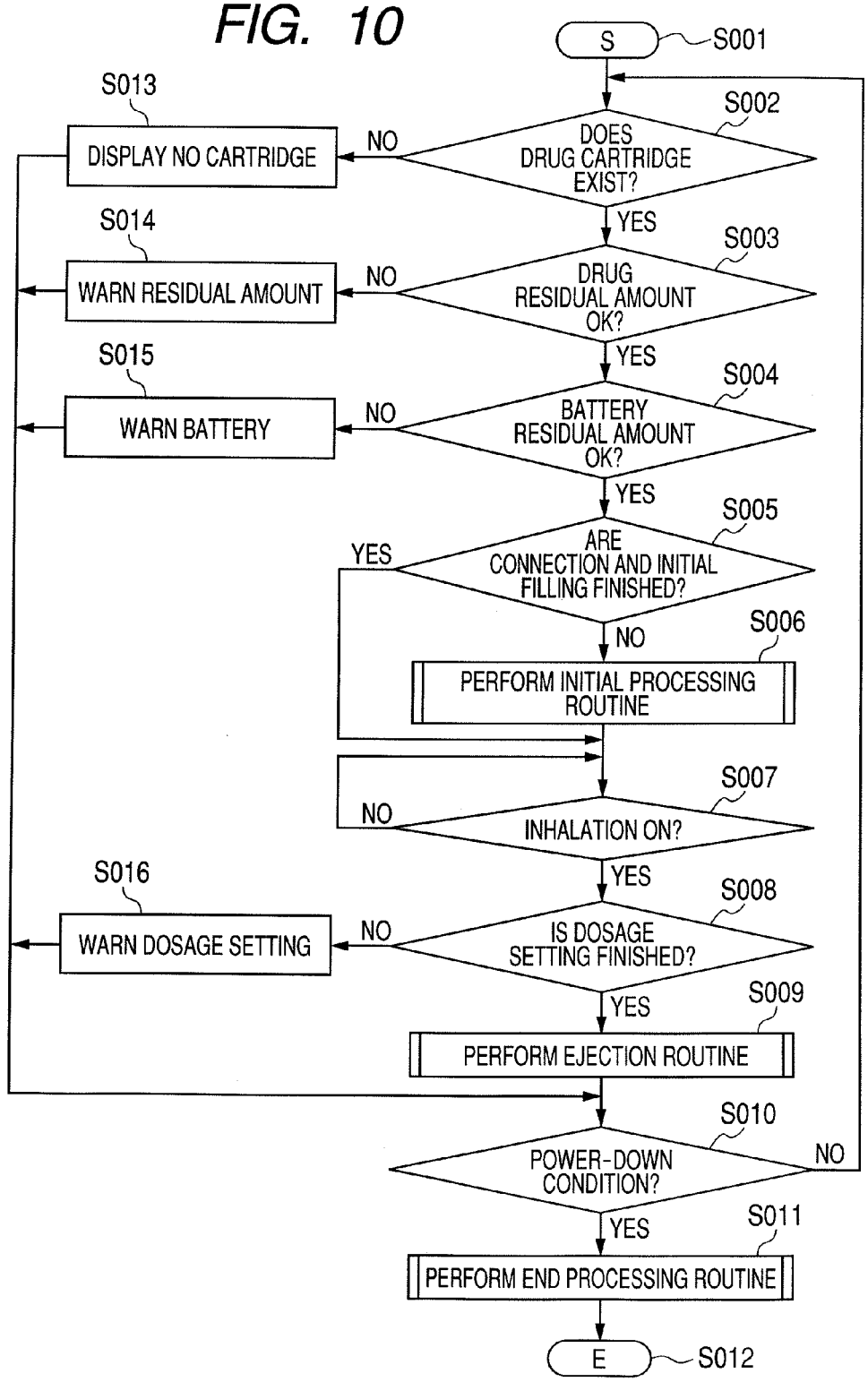
FIG. 10 is a flowchart illustrating an example of the overall operation of the inhaler.

FIG. 10 is a flowchart illustrating an example of the overall operation of the inhalation apparatus. When the power source is turned on with the power switch 112, the operation starts from step S001. First, it is determined whether a drug cartridge is mounted in the cartridge detection sensor 113. When it is not mounted, display of no cartridge is performed (S013), and when it is mounted, it goes into determination of drug residual amount (S002). When the drug residual amount is insufficient, a residual amount warning is given (S014), and when the drug residual amount is enough, it goes into determination of battery residual amount (S003). For the determination of the drug residual amount, a software-like method can be used. That is, it is determined whether the liquid measure obtained by subtracting the full dosage, used for the past, from the first medical fluid amount is larger than maximum ejection amount in the following ejection. If the drug residual amount is determined to be sufficient in step S003, the processing goes into determination of battery residual amount, if residual amount is insufficient, a battery warning is performed (S015), and if the residual amount is sufficient, the processing goes to a routine for ejection after S005 (S004).

Since an ejection head is not filled with drug yet if the drug cartridge is mounted newly, it is necessary to perform a filling treatment of the drug. Determination of whether the drug cartridge detected is a new article, is achievable by recording last information on the drug cartridge on a noncontact IC tag and reading it. As another method, the determination can be made by reading the position of the movable wall of the drug tank optically, and using the positional information. As for still another method, it can be also performed to fold a pawl member attached to a part of a housing of the cartridge when initial filling is completed.

When it is determined at S005 to be a drug cartridge that the initial filling has already ended, it skips an initial processing routine S006, and it goes into the determination of timing waiting of inhalation (S007). At the initial processing routine S006, initial filling of a drug to the head mentioned later and an operation for negative pressure securement for preparing the following spraying are performed. Nevertheless, even when it is determined to be a drug cartridge in which the initial filling has ended, when a restoring operation is performed every use, the initial processing routine (S006) can be performed. Here, when the initial processing routine S006 is performed after the power source is turned on, it is suitable to provide inhibition means of inhibiting ejection of a drug unless it is completed.

When a user's inhalation start is detected at S007, it goes into determination of whether a predetermined dosage necessary for spraying has been already set (S008). Dosage setting is performed by the up button 12, down button 13, and determination button 14 which are described in FIG. 2. If the dosage is fixed each time, the setting value performed in the past is made the dosage. If the setting has not been performed at S008, a patient is warned to set the dosage (S016), and if the setting has been already performed, it goes to an ejection routine (S009).

After the ejection is completed at the ejection routine S009 mentioned later, it is determined whether it is a power-down condition (S010). Here, the condition for determination of a power-down may be to detect that a user operated the power switch 112, or the power-down may be performed each time when medication is completed. Furthermore, when determination of a low battery state is made, the power-down may be performed. When it is the power-down condition at S010, it goes to an end processing routine (S011).

Figure 11:
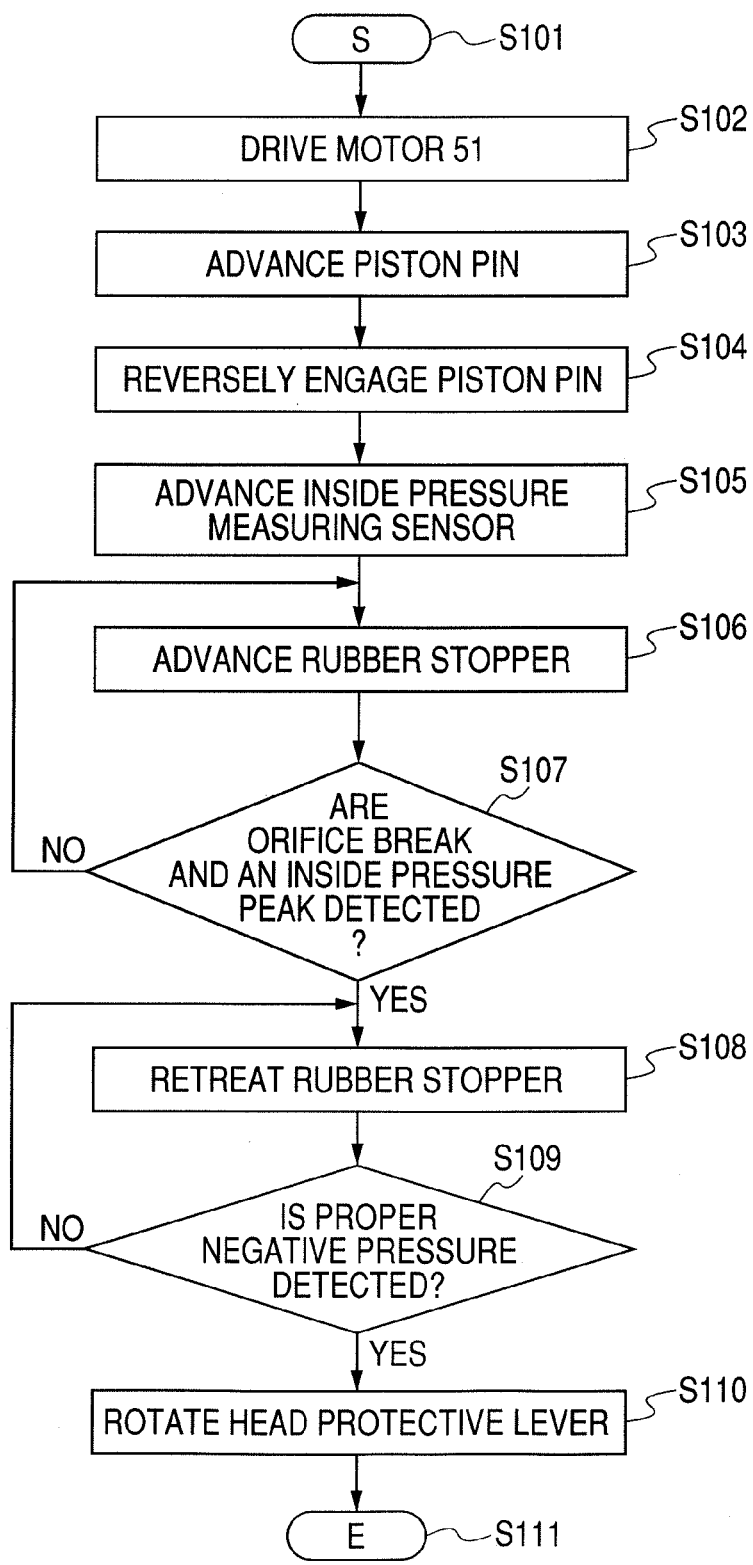
FIG. 11 is a flowchart of an initial processing routine S006 in FIG. 10.

FIG. 11 describes the initial processing routine S006 in FIG. 10 which is a feature of the control method of a drug ejecting apparatus of the present invention in order of steps. The motor 51 is driven and the ejection head unit 1 and drug tank 2 are made to communicate (S102). The drug pass 42 to which the drug passes along the hollow needle 38 and flows into the ejection head 8 is formed. Next, in order to make the piston pin 61 connect to the moving rubber stopper 34, it is made to advance by certain amount toward the moving rubber stopper 34 (S103). The certain amount means movement amount of an end portion of the piston pin 61 contacting the moving rubber stopper. Since the screw shaft motor 64 is using the step motor, the movement amount is controllable by the number of steps converted from a distance to contact.

Next, the piston pin reverse motor 71 is made to be driven, and a piston shaft tip unit rotates by 90° so as to engage with the moving rubber stopper joint 45 (S104). Next, the motor 81 is made to be driven in order to advance the pressure sensor 43 (S105). The pressure sensor 43 enters into the pressure detection opening 23, is stuck to the sealant 22, and prevents a pressure leak. An adhesion force of the sealant 22 and pressure sensor 43 is generated by a return spring force of the connection pressure spring 86.

Next, it goes to a step of filling the drug 32 into the ejection head 8. The piston pin 61 is advanced and the moving rubber stopper 34 is moved in a direction in which the inside volume of the glass container 33 is reduced. Then, the drug 32 inside the glass container 33 flows into an inside of the ejection head 8 through the drug pass 42, air in the drug pass 42 is pushed out from the ejection port, and an interior of an ejection head 8 is filled with the drug (S106). However, since the diameter of an ejection nozzle 1a is as small as 3 µm, pressure in the drug pass and glass tube starts to rise without the drug leaking out immediately. A pressure change is measured and it is fed back to movement control of the moving rubber stopper 34 (S107).

Figure 12:
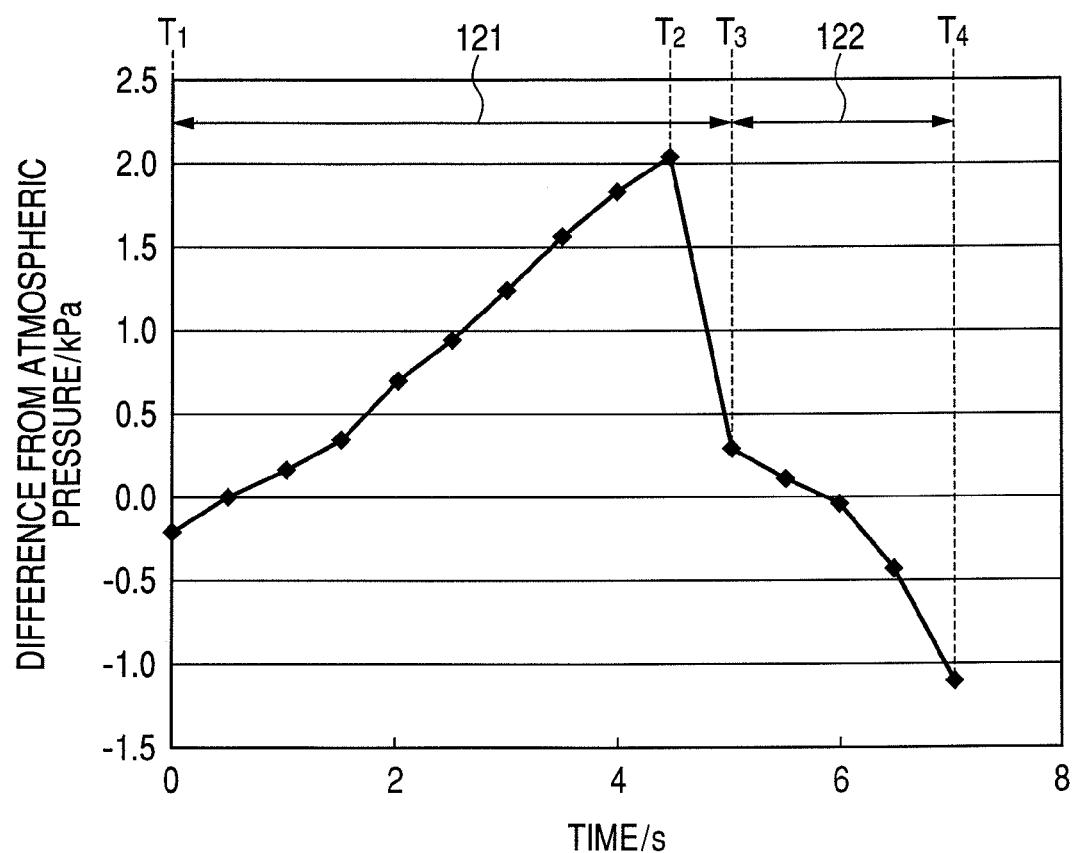
FIG. 12 is a graph illustrating a pressure change in a drug tank at the time of filling.

The pressure change in the drug tank at the time of this filling is illustrated in FIG. 12. An arrow 121 is a pressurized process, and 122 is a depressurized process. When the piston pin 61 is advanced from time T1, inside pressure rises gradually. It is turned out from an experiment that, in Φ3 µm of ejection nozzle, a meniscus is torn near 2 kPa and the medical fluid leaks out. Furthermore, when the piston pin 61 is advanced, the meniscus is torn near 2 kPa (time T2), and when the medical fluid leaks out, it appears in the pressure sensor that inside pressure drops suddenly (time T3).

In this way, when it is determined that the initial filling is completed at S107, an operation for initial negative pressure securement is started next. The screw shaft motor 64 is rotated so that the rubber stopper 34 may be made to slide in a direction in which volume inside the tank increases, and the rubber stopper 34 is retreated (S108). When the rubber stopper is retreated until proper negative pressure is detected with the pressure sensor 43, the initial processing routine is ended (S109). These operations will be illustrated in FIG. 12. Reverse rotation of motor drive is performed from the time T3, and it reaches at −1.0 kPa, which is proper negative pressure, at the time T5. Since the initial filling and securement of negative pressure are completed now, the head protective lever 21 is rotated for the first ejection (S110). The drug which leaks out is sucked and absorbed by the drug absorber 35 provided inside the head protective lever. In this way, when the pressure sensor 43 for measuring pressure in the drug tank 2 is provided, the filling operation and initial negative pressure securing operation of the present invention can be monitored with sufficient accuracy.

Figure 13:
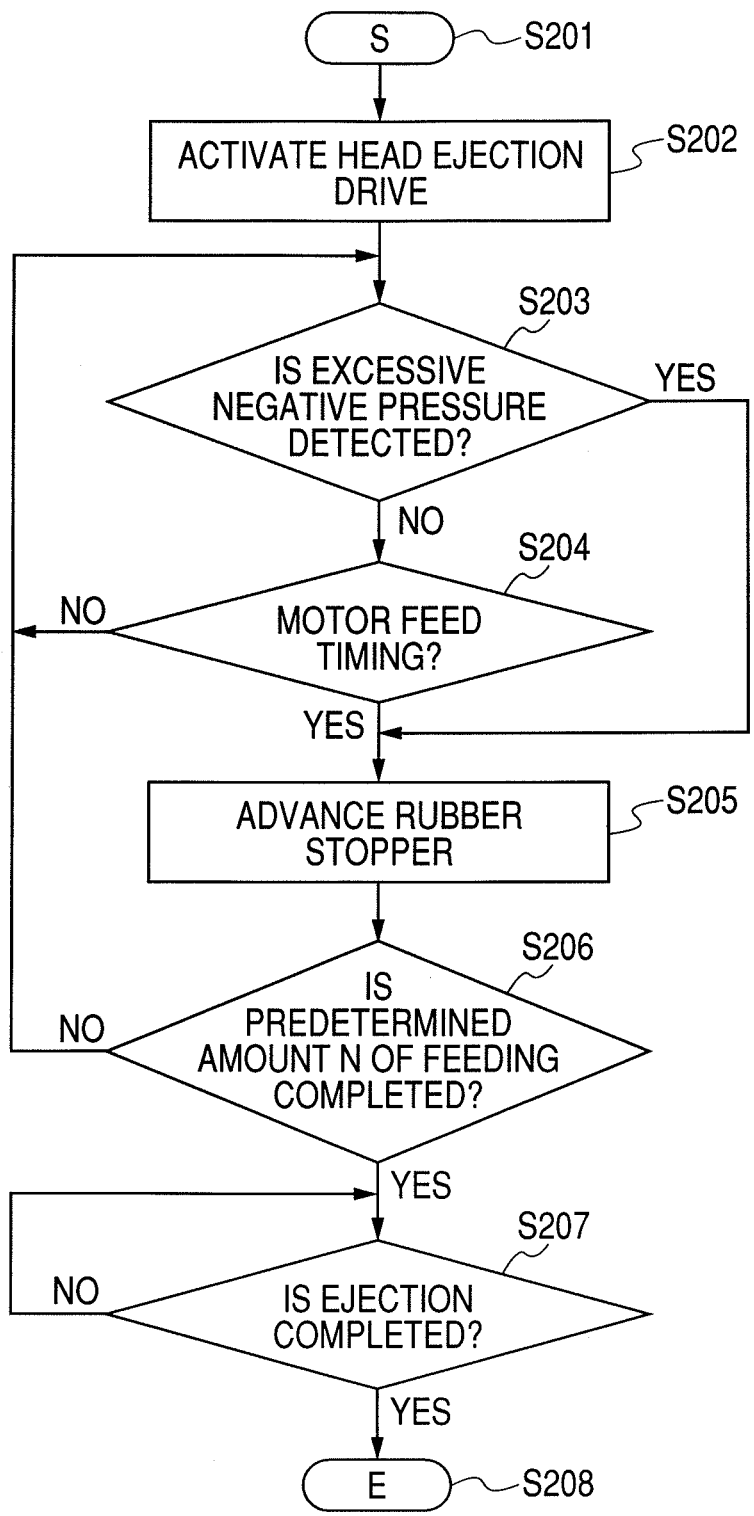
FIG. 13 is a flowchart of an ejecting routine S009 in FIG. 10.

FIG. 13 illustrates the ejection routine S009 in FIG. 10 in detail. When it goes to the routine from S201, head ejection is activated first (S202). Here, according to parameters for the control unit 4 to perform a head drive, a start for ejection is performed to the head drive circuit 110. Parameters are specifically an ejecting operation period, a head drive frequency, a pulse width, and a drive voltage. The ejecting operation period is time to a last pulse being generated completely from the first pulse given to the drive element of the ejection head in one medication. In addition, the head drive frequency is equivalent to the number of pulse signals given to the respective drive elements of the ejection head per unit time. The pulse width is application time in one pulse signal application, and the drive voltage is an applied voltage given to the ejection energy generating element. These parameters enable to determine the ejection amount per unit time, and the dosage per time.

When it is determined from a detection value of the pressure sensor that it is not excessive negative pressure (S203), it is determined whether it is the timing corresponding to ejection medical fluid amount (S204), and the screw shaft motor 64 is sent out by one step (S205). Operations from S204 to S205 are repeated by predetermined amount N (S206), and after the completion, the ejection routine is completed on the condition that the drive in the head drive circuit 110 is completed (S207).

Figure 14:
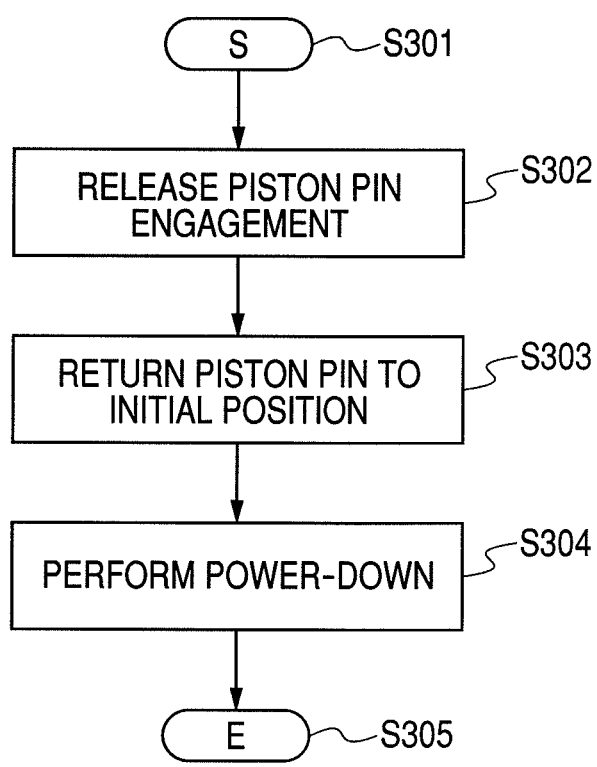
FIG. 14 is a flowchart of an end processing routine S011 in FIG. 10.

FIG. 14 illustrates the end processing routine S011 in FIG. 10. When it goes into the routine from S301, in order to separate a moving rubber stopper joint 45 from a piston, the motor 71 is rotated in a direction reverse to that at the time of the initial processing routine, and engagement is released (S302). After that, the piston pin 61 is returned to the initial position so that the cartridge can be removed by the motor 64 (S303). After that, an operation for the control unit 4 to turn off a power supply circuit is started (S304). In performing the power-down, data of an apparatus state necessary at the time of a next startup of the apparatus system, and the like are made to be stored suitably in nonvolatile memory mounted in the control unit 4.

Second Embodiment

Next, a second embodiment of performing operations without measuring drug tank inside pressure will be described.

Figure 15:
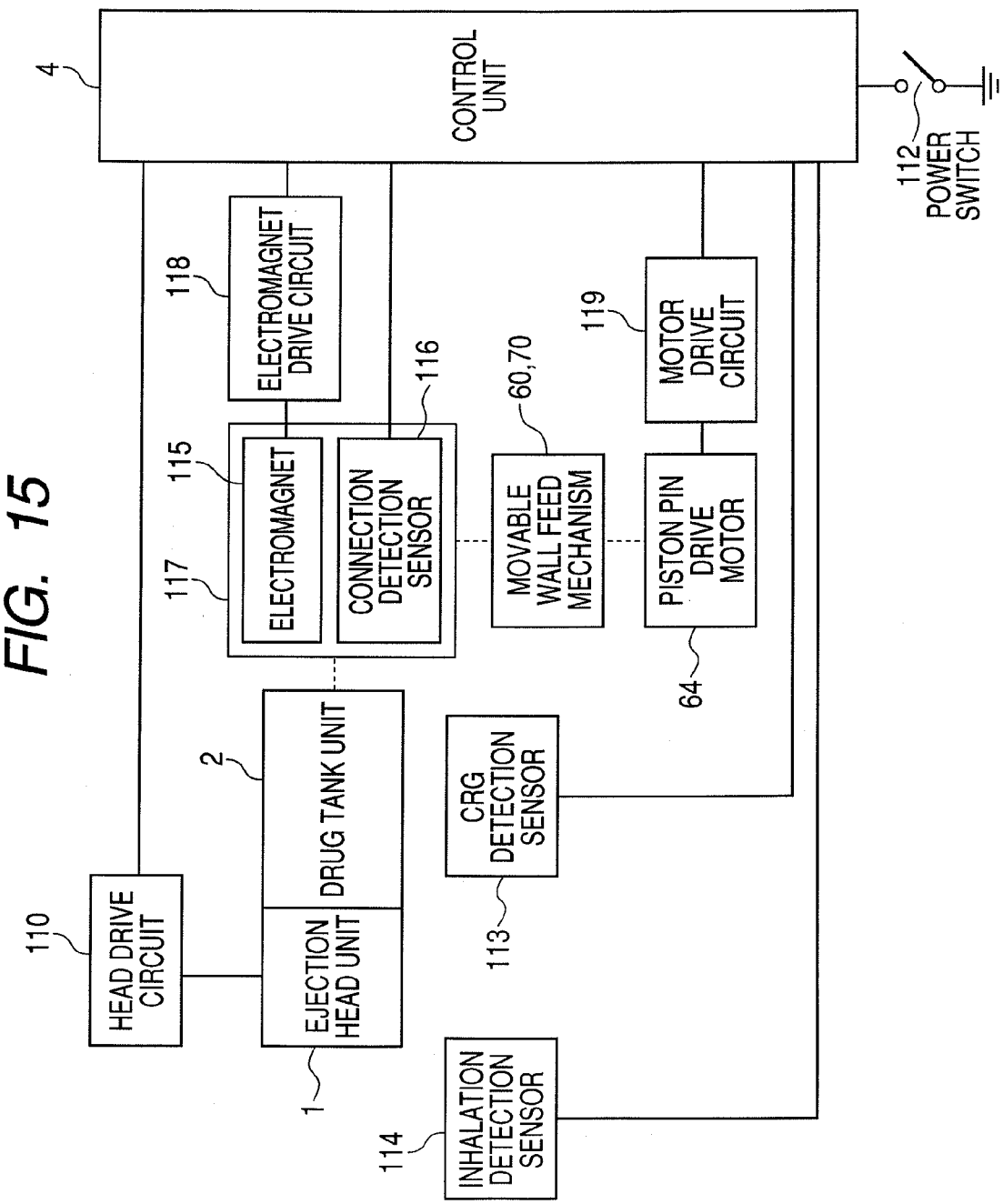
FIG. 15 is a block diagram of an inhalation apparatus according to a second embodiment.

FIG. 15 is a block diagram of an inhalation apparatus according to the second embodiment. In this embodiment, instead of the moving rubber stopper joint 45 which is a function to adjust inside pressure of the drug tank, an electromagnet is used for connection to be achieved. As to construction, there is a connecting unit 117 which interlocks with the movable wall feed mechanism and moves, and inside it, a connection detection sensor 116 which detects that the piston pin was sent to the piston position in the drug tank 2 is incorporated. It detects that the connection sensor 116 contacts the rubber stopper 34 which faces it. For that reason, in the rubber stopper 34, a member which is a material like iron which is electroconductive and is attracted by a magnet is unified and constructed.

Figure 16:
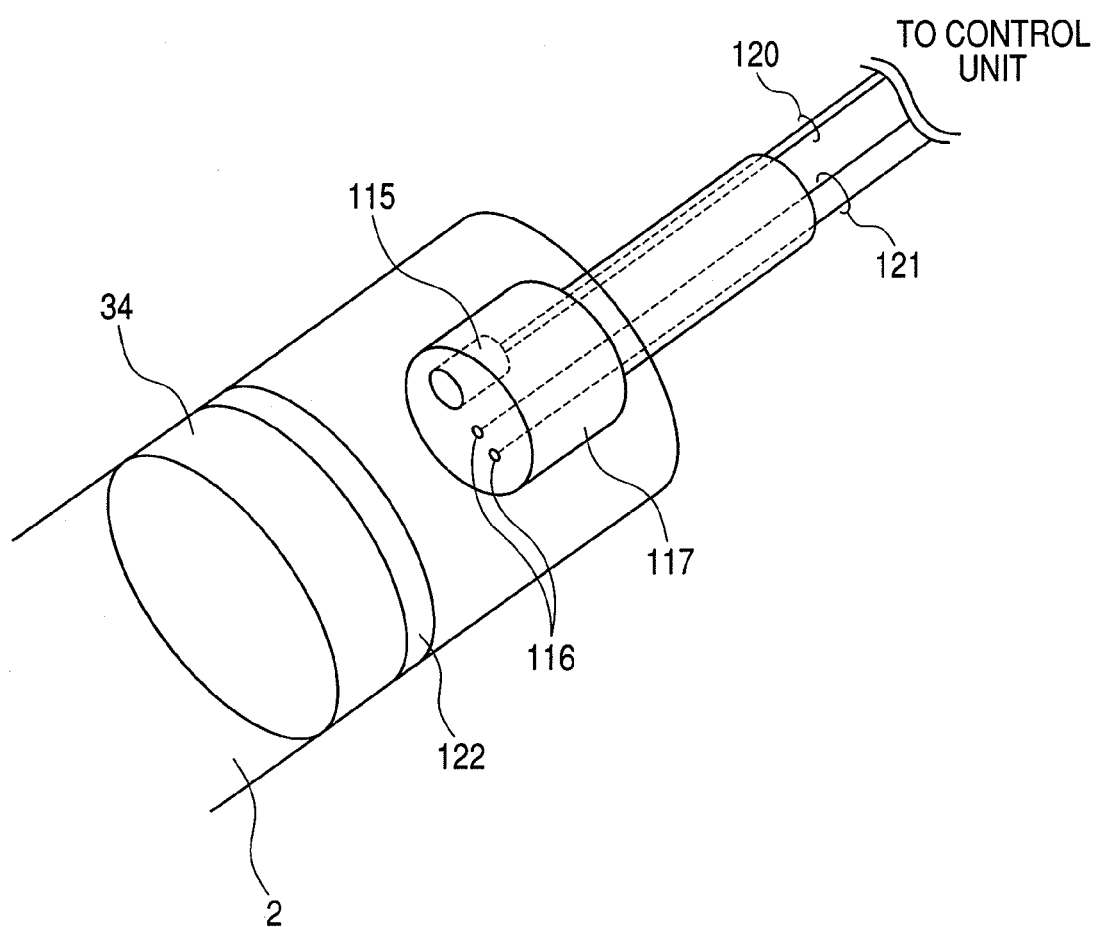
FIG. 16 is a conceptual drawing of the vicinity of a connecting unit 117 in FIG. 15.

FIG. 16 illustrates surrounding construction of the connecting unit 117. In the rubber stopper 34, an adsorption plate 122 which is made from a material which is adsorbable adsorb to a magnet, for example, a metal is constructed in one piece. A contact terminal is buried in the connecting unit 117, and is installed in a position in which conduction occurs when the connecting unit 117 contacts the adsorption plate 122. When an end face of the connecting unit 117 contacts the adsorption plate 122, it is detected in the control unit 4 through a connection sensor line 121. An electromagnet 115 is further mounted in the end face of the connecting unit 117, and is given current drive by an electromagnet drive circuit 118 through an electromagnet drive line 120.

Figure 17:
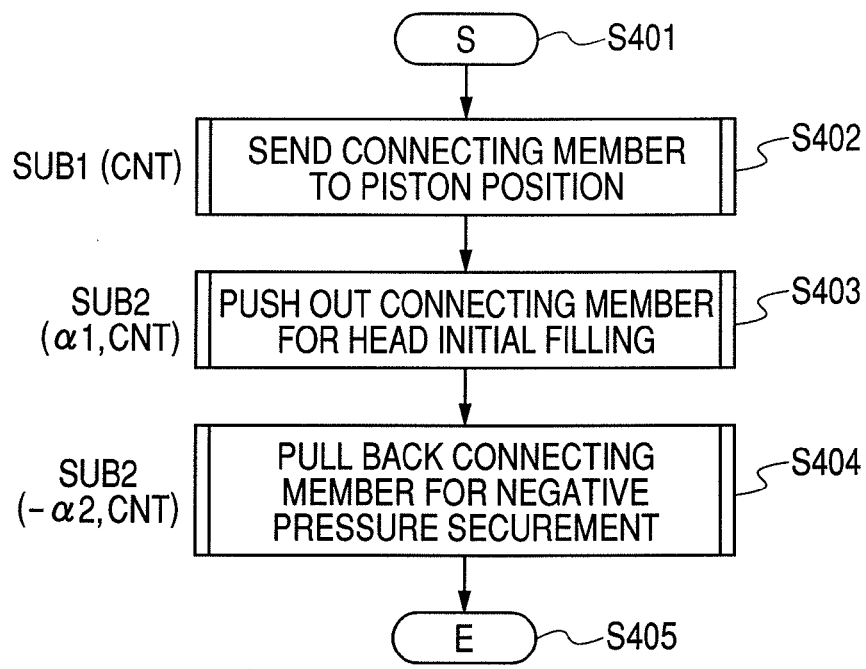
FIG. 17 is a flowchart of an initial processing routine in the second embodiment.

FIG. 17 illustrates a flow of the initial processing routine S006 in FIG. 10. After starting from S401, a subroutine (SUB1) for sending the connecting unit 117 and making it connected to a sending piston is activated (S402). At this time, a connecting unit position (CNT) at that time is input as an argument. Since the connecting unit is retreated to the initial position at the time of the initial filling, it is made to be CNT=0. When connection is completed at S402, in order to perform extrusion for ejection head initial filling, a subroutine (SUB2) is activated, and the ejection head is made to be filled with the drug (S403). Next, in order to prepare for the first ejection and to secure negative pressure, the subroutine (SUB2) is activated (S404). The SUB2 drives a stepping motor equivalently to the desired number of steps, and hands over the number of steps (N) and the present connecting unit position CNT to be needed as arguments. The number of steps ($\alpha$1) necessary for the head initial filling is used at S403, and the number of steps ($-\alpha$2) necessary for negative pressure securement is done at S404. These numbers of steps are beforehand determined in consideration of dimension dispersion of a product, or installation dispersion of a cartridge in a development stage as numerical values with which operations are securely warranted. According to an experiment, it is confirmed that the time of initial filling is performed with 50 µL. Let the inner diameter of the glass container be 10.5 mm and let the moving distance (=moving distance of stepping motor) of the movable wall be d (mm), the following holds:

$$50\ \mu L = \pi \times (10.5\ mm/2)^2 \times d\ mm$$

since the pulse number needed for the stepping motor moving by 1 mm is 161, it is set at $\alpha$1=91. In addition about the $\alpha$2, it turns out that proper negative pressure (−1 to −5 kPa) is achievable at $\alpha$2=3.

Figure 18:
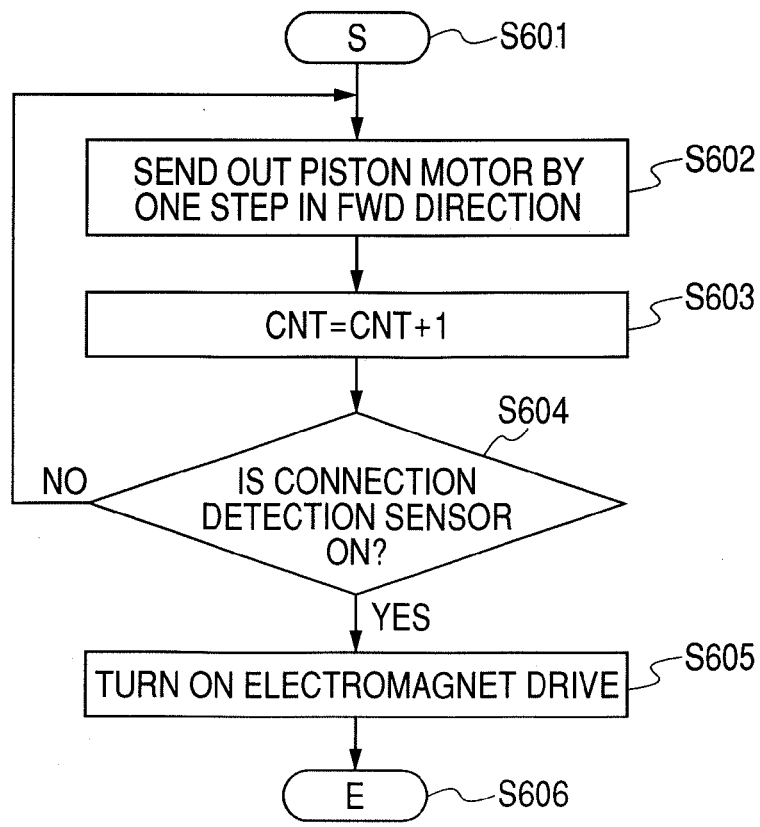
FIG. 18 is a flowchart of a subroutine of performing a connecting operation of the connecting unit 117 and a piston in the second embodiment.

FIG. 18 illustrates a flow of the subroutine SUB2 for connection. The piston motor is sent equivalently to one step in a positive direction FWD after being activated at S601 (S602), and the stepping motor position CNT is counted up by one (S603). This operation is repeated until the connection sensor 116 contacts it (S604), and the electromagnet is driven when it is detected (S605).

Figure 19:
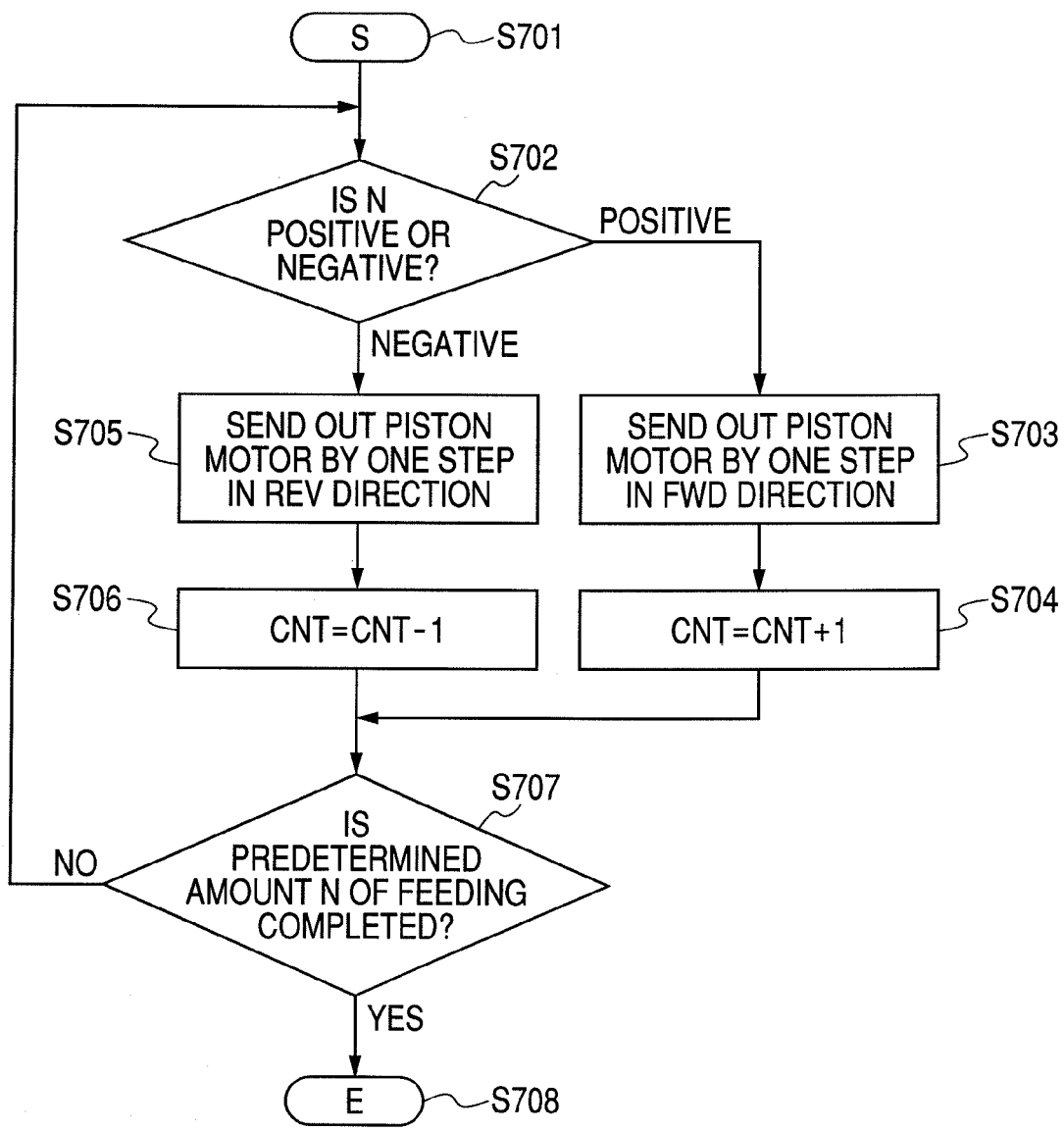
FIG. 19 is a subroutine for sending the connecting unit 117 by specified steps in the second embodiment.

FIG. 19 illustrates a flow of the subroutine SUB2 for piston motor feeding. After it is activated at S701, according to a designated argument N, it is determined whether it is the positive direction FWD or a negative direction REV (S702). As for the argument N, a positive integer is designated when it is the positive direction, that is, a direction of sending out the piston, and a negative integer is designated when it is the negative direction, that is, a direction of pulling back the piston. The piston motor is sent equivalently to one step in the positive direction when it is the positive direction (S703), and the stepping motor position CNT is counted up by one (S704). The piston motor is pulled back equivalently to one step in the negative direction when it is the negative direction (S705), and the stepping motor position CNT is counted down by one (S706). The routine is ended after repeating this operation equivalently to the predetermined amount N (S707). The stepping motor position CNT is returned as a variable.

In this way, a storage unit which stores displacement amount of the movable wall for the filling operation and initial negative pressure securing operation which are determined beforehand is provided in the control unit 4. By displacing the movable wall 3 based on this information, the simple construction which does not provide the pressure sensor 43 for inside pressure measuring is achievable. In addition, it is suitable to make changeable the displacement amount at the time of displacing the movable wall 3 for an initial negative pressure securement according to the drug residual amount so as to secure comparable negative pressure each time.

Figure 20:
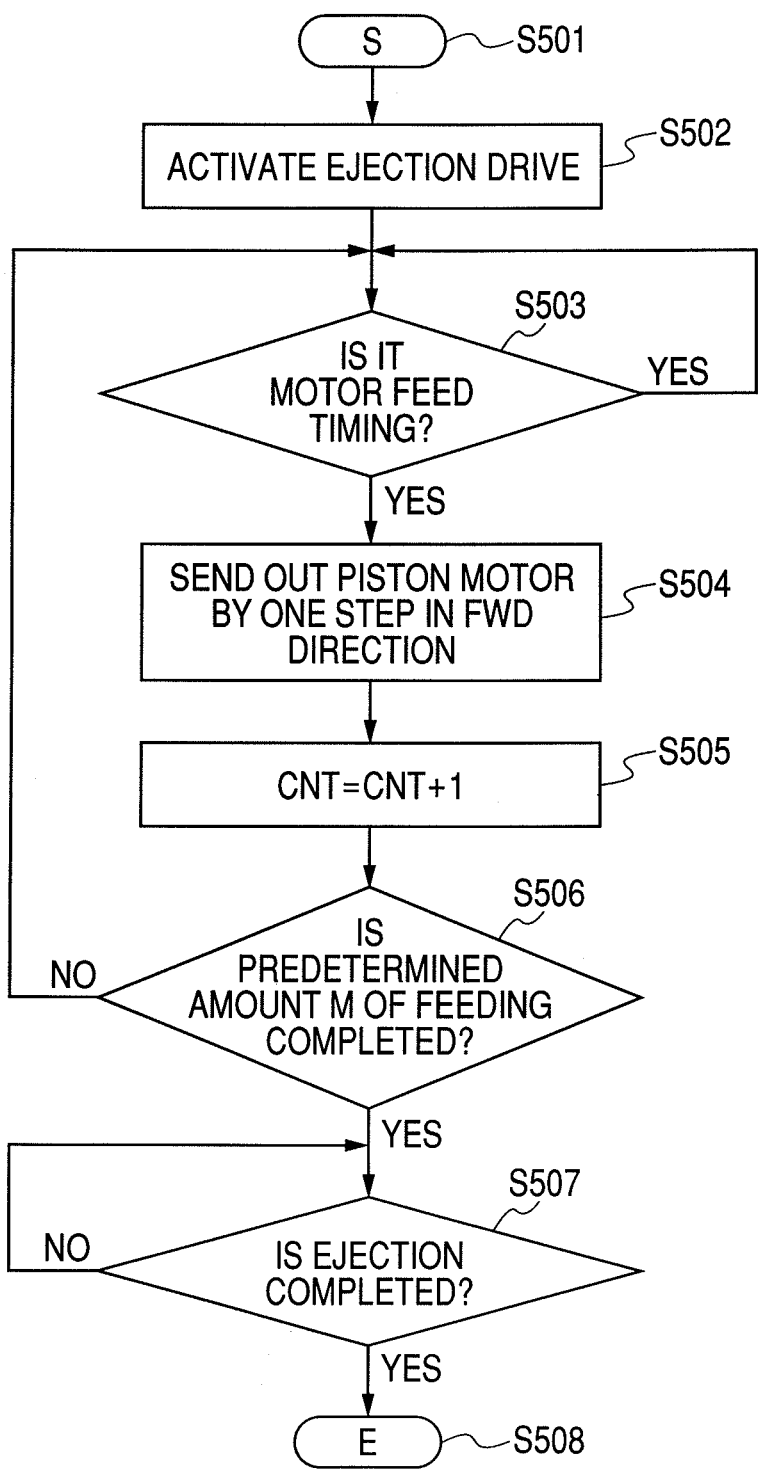
FIG. 20 is a subroutine for performing step feed of the connecting unit 117 with synchronizing it with ejection timing in the second embodiment.

FIG. 20 illustrates a flow of the ejection routine S009 in FIG. 10. After being activated at S501, the head drive circuit 110 which follows the head drive parameters is activated from the control unit 4 (S502). Next, since the drug ejection volume per unit time is determined from the head driving parameter mentioned above, it is necessary to perform a synchronous drive of the motor 64 for connecting unit feeding according to the volume and to send out it. This is because tank inside pressure is always kept within proper limits by matching the medical fluid volume per unit time which is ejected from the head, and delivery amount of the connecting unit while the ejection is performed. Feed timing of the piston pin drive motor 64 may be just the time when the ejection head ejects the volume corresponding to drug extrusion capacity of the stepping motor equivalently to one pulse (S503). The piston motor is sent equivalently to one step in the positive direction FWD when the time elapsed (S504), and the stepping motor position CNT is counted up by one (S505). The routine is repeated until this operation is performed by M times of necessary dosage (S506). It is activated at S502 after that, completion of the ejecting operation in the head drive circuit which operates independently is confirmed, and the routine is ended when it is completed (S507). The stepping motor position CNT is returned as a variable.

Specific numerical examples will be shown below. Here, the drug tank used in an experiment will be calculated as an example. Let an inner diameter of the glass container be 10.5 mm, and let ejection be 20 µL/second, and let a piston moving length per unit time be d mm/second, and it becomes d=0.227 mm/second from 20 µL/second=$\pi \times (10.5\ mm/2)^2 \times d$ mm/second.

Since the pulse number needed for the stepping motor, used in the experiment, moving by 1 mm is 161, this means that it may be sent at 36.5 pulses per second, that is, 27 milliseconds per one pulse on a time basis. Here, let a dosage per time be 50 µL, and the full feed pulse number M becomes 91.

INDUSTRIAL APPLICABILITY

The drug ejecting apparatus of the present invention may be used for various uses besides for drug inhalation. For example, it can be also used for a spray form ejecting apparatus of aromatics and the like, an inhalation apparatus of luxury goods, such as nicotine, and the like. Thus, the drug ejecting apparatus of the present invention is applicable to various use which needs certain and sanitary ejection.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications Nos. 2008-014458, filed Jan. 25, 2008, and 2008-157987, filed Jun. 17, 2008, which are hereby incorporated by reference herein in their entirety.

The invention claimed is:

1. A drug ejecting apparatus comprising:
a drug ejection apparatus which has an ejection port and an element which generates energy for ejecting a drug from the ejection port;
a drug containing unit which is connected to the drug ejection apparatus, and contains the drug;
a movable wall which is attached to an end of the drug containing unit, and is displaced by a difference between pressures from the inside and outside of the drug containing unit; and
a control unit which displaces the movable wall, wherein the drug ejection apparatus is filled with the drug, and inside pressure of the drug containing unit is made into a negative pressure state in advance of ejecting of the drug, by displacing the movable wall by means of the control unit.

2. The drug ejecting apparatus according to claim 1, further comprising an inhibition unit which inhibits ejection of a drug from the drug ejection apparatus before making inside pressure of the drug containing unit into a negative pressure state by displacing the movable wall.

3. The drug ejecting apparatus according to claim 1, further comprising a storage unit which stores a displacement amount of the movable wall for filling the drug into the drug ejection apparatus, and a displacement amount of the movable wall for making inside pressure of the drug containing unit into a negative pressure state, and wherein the control unit displaces the movable wall based on the displacement amount stored in the storage unit.

4. The drug ejecting apparatus according to claim 1, wherein displacement amount of the movable wall is made changeable according to drug residual amount inside the drug containing unit.

5. The drug ejecting apparatus according to claim 1, wherein the drug ejection apparatus ejects the drug by an ejection principle of an ink jet system.

6. A drug ejecting apparatus, comprising:
   a drug ejection apparatus which has an ejection port and an element for ejecting a drug from the ejection port by an ejection principle of an ink jet system;
   a drug containing unit which is connected to the drug ejection apparatus, and contains the drug;
   a movable wall which is attached to an end of the drug containing unit, and is displaced by a difference between pressures from the inside and outside of the drug containing unit;
   a storage unit which stores displacement amount of the movable wall for filling the drug into the drug ejection apparatus, and displacement amount of the movable wall for making the inside pressure of the drug containing unit into a negative pressure state according to a drug residual amount inside the drug containing unit; and
   a control unit which has an inhibition unit for inhibiting ejection of the drug from the drug ejection apparatus, and displaces the movable wall,
   wherein the control unit fills the drug ejection apparatus with the drug, and makes the inside pressure of the drug containing unit into a negative pressure state in advance of ejection of the drug, by displacing the movable wall based on the displacement amounts stored in the storage unit, and
   wherein the control unit inhibits ejection of the drug from the drug ejection apparatus before making the inside pressure of the drug containing unit into a negative pressure state, and keeps the negative pressure state inside the drug containing unit while ejection of the drug is performed.

* * * * *